United States Patent [19]

Michaels

[11] Patent Number: 4,464,316

[45] Date of Patent: Aug. 7, 1984

[54] NON-REFILLABLE HUMIDIFIER CONTAINER

[75] Inventor: Thomas L. Michaels, Wonder Lake, Ill.

[73] Assignee: Baxter Travenol Laboratories, Inc., Deerfield, Ill.

[21] Appl. No.: 401,297

[22] Filed: Jul. 23, 1982

[51] Int. Cl.³ .............................................. B01F 3/04
[52] U.S. Cl. ........................... 261/121 R; 128/200.11; 215/216; 215/218; 215/221; 261/DIG. 65
[58] Field of Search ................. 261/121 R, DIG. 65; 215/216–218, 221, 341, 252; 128/200.11

[56] References Cited

U.S. PATENT DOCUMENTS

| | | | |
|---|---|---|---|
| 3,185,333 | 5/1965 | Sharp | 215/216 |
| 3,233,769 | 2/1966 | Jessop | 215/216 |
| 3,770,153 | 11/1973 | Gach et al. | 215/216 |
| 3,826,395 | 7/1974 | Montgomery | 215/341 X |
| 3,841,514 | 10/1974 | Montgomery et al. | 215/216 |
| 3,846,518 | 11/1974 | McPhee | 261/DIG. 65 |
| 3,877,597 | 4/1975 | Montgomery et al. | 215/221 |
| 3,880,314 | 4/1975 | Akers | 215/216 X |
| 3,941,268 | 3/1976 | Owens et al. | 215/216 |
| 3,984,021 | 10/1976 | Uhlig | 215/216 |
| 4,036,919 | 7/1977 | Komendowski et al. | 261/DIG. 65 |
| 4,062,466 | 12/1977 | Conti | 215/252 |
| 4,345,690 | 8/1982 | Hopley | 215/216 |

Primary Examiner—Richard L. Chiesa
Attorney, Agent, or Firm—Paul C. Flattery; John A. Caruso; Garrettson Ellis

[57] ABSTRACT

A closure system for a non-refillable container is provided. In the system, an internally threaded cap is carried in threaded cooperation on the neck of the container. Removal of the cap from a capped container is prevented through a combination of locking lugs and camming ramps having end stops. Locking lugs can be either on the cap or on the container neck with corresponding camming ramps located, respectively, on either the container neck or the cap. The locking lugs radially flex over the camming ramps as the cap is screwed onto the neck and radially snap back when out of camming relation with the camming ramp. Removal of the cap is prevented by contact of the locking lugs with the end stops of the camming ramps when the cap is attempted to be removed.

17 Claims, 9 Drawing Figures

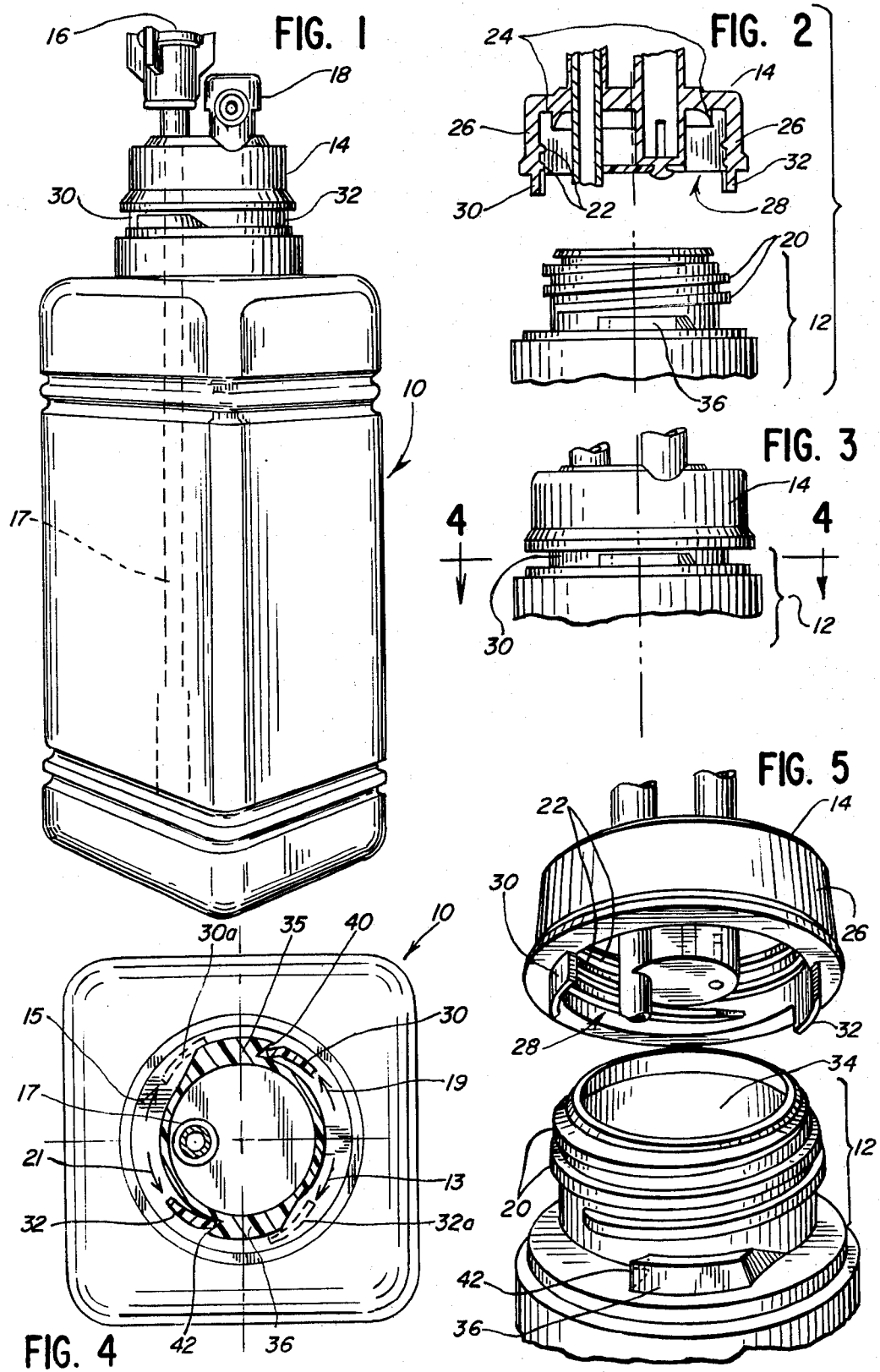

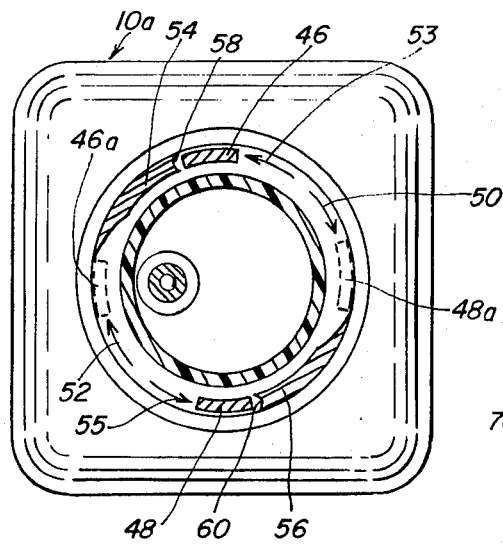
FIG. 6
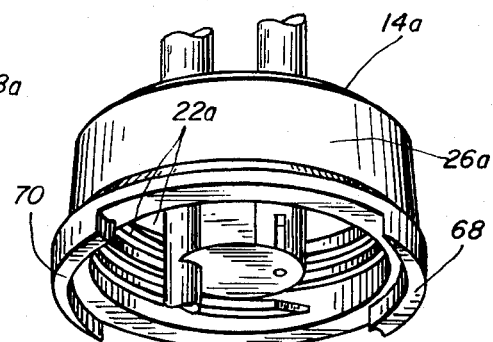
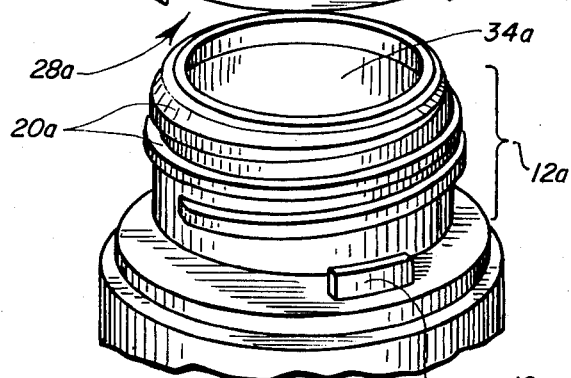
FIG. 7
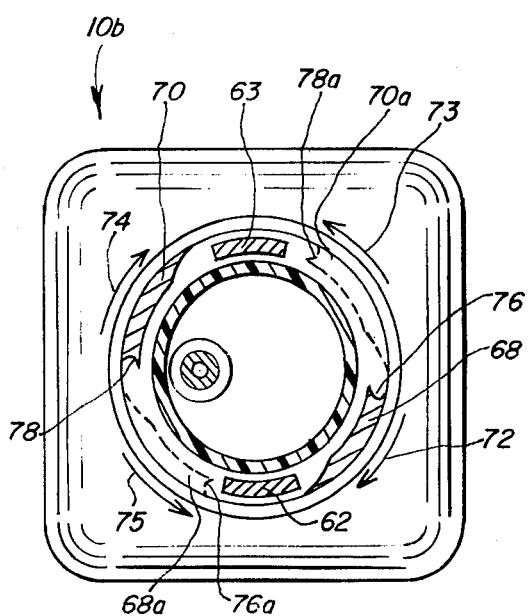
FIG. 8
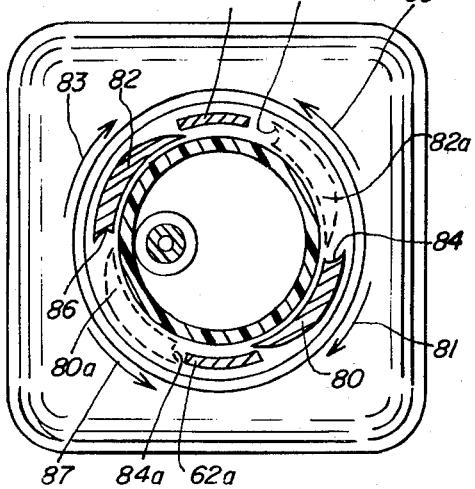
FIG. 9

NON-REFILLABLE HUMIDIFIER CONTAINER

FIELD OF THE INVENTION

This invention relates to locking caps and closure systems for containers. The invention particularly relates to an irremovable locking cap for filled containers where the container is intended to be non-refillable. An example of such a non-refillable container is a humidifier bottle used in respiratory therapy where contamination of the humidifying solution in the bottle is minimized by using an irremovable locking cap.

BACKGROUND OF THE INVENTION

The container industry, the closure industry, and other industries engaged in the manufacture and sale of products desirably contained safely, that is out of reach or inaccessible by children, have developed many so-called "child-proof" or "child-resistant" caps or closures. Many of these closures use the combination of a camming projection or ramp and a locking lug. The combination may include locking lugs located on the cap and camming ramps located on the container neck. Alternatively, the lugs may be located on the neck of the container with the camming ramps located on the container cap. Ratchet type arrangements are also popularly used on "child-proof" containers.

A representative "child-proof" cap may be found in U.S. Pat. No. 3,877,597 to Montgomery et al., for "CHILD-RESISTENT CLOSURE FOR LIQUID CONTAINERS". Montgomery discloses a child-proof bottle having an extending lug and an inclined ramp. The cap of the bottle includes a liner underlying its top, adapted to be compressed against the neck of the container at its outlet when the two are engaged. Disengagement of the locking arrangement is accomplished by raising the extending lug. U.S. Pat. No. 3,233,769 to Jessop, for "SCREW-CAPPED CONTAINERS AND SAFETY DEVICES THEREFOR", U.S. Pat. No. 3,880,314 to Akers, for "CONTAINER AND SAFETY CAP", and U.S. Pat. No. 3,941,268 to Owens et al., for "SAFETY CLOSURE AND CONTAINER" all disclose containers, including screw-on caps with container assemblies, where inclined ramp and lug arrangements are used to prevent opening of the containers. Each container is provided with means for disengaging the ramp and lug engagement.

Moreover, U.S. Pat. No. 3,770,153 to Gach et al., for "SAFETY CLOSURE", U.S. Pat. No. 3,826,395 to Montgomery, for "LEAK-PROOF CLOSURE FOR A LIQUID CONTAINER", U.S. Pat. No. 3,841,514 to Montgomery et al., for "SAFETY CLOSURE", and U.S. Pat. No. 3,984,021 to Uhlig, for "SAFETY CLOSURE CONTAINER" disclose downwardly depending locking lugs used with camming projections or ramps and further disclose containers with side wall recesses which accommodate the downwardly depending lugs on the periphery of the cap skirts. Again, each of these cap and container configurations is provided with means for disengaging the locking engagement that exists when the container is closed by the cap.

By this invention, a closure system for a non-refillable container is provided. Once the cap of the closure system is threaded onto the neck of the container, removal of the cap is prevented. The feature of having an irremovable cap discourages a user from refilling the container with a contaminated or improper solution.

BRIEF SUMMARY OF THE INVENTION

The present invention provides a closure system for a non-refillable container. The container includes a neck defining an outlet and having external threads. A cap having corresponding internal threads is carried on the neck of the container. Through a system of locking lugs on the cap and camming ramps having end stops on the container or camming ramps on the cap and locking lugs on the container, the cap of the closure system is made irremovable and the container is made non-refillable. Unlike currently used locking "child-proof" containers, irremovability of the locking cap of this invention is assured. The use of locking lugs that are strong enough to be substantially free of tangential flex when the cap is rotated under hand pressure prevents the removal of the cap in this manner. Irremovability of the cap under squeezing, hand force is further insured by the cap being strong enough to resist lateral deflection of a type to cause locking lugs or camming ramps on the cap to laterally deflect. That is, squeezing of the cap will not alter the locking relationship of the lugs and the camming ramps.

In the preferred embodiment, the closure system of this invention is used for a non-refillable, humidifier container where the container is filled with a respiratory therapy solution for inhalation therapy. The cap of the present closure system defines a skirt having an open end. The cap has at least one locking lug extending downwardly from the open end of the skirt. The closure system and container are non-refillable in the sense that direct access to the container contents through the container outlet is not possible once the cap is locked in place.

At least one camming ramp, which terminates in an end stop, is located on the container neck. The camming ramp is positioned on the container neck and proportioned to flex the depending locking lug over the end stop as the cap is screwed onto the neck. When the locking lug advances past the end stop of the cam, the locking lug will snap radially inward, out of camming relation with the camming ramp. The proportions of the locking lugs are such that when one attempts to remove the cap, the depending locking lug or lugs will not flex substantially tangentially, thereby preventing removal of the cap.

In the preferred embodiment the cap has an inlet connected to a gas permeable dip tube manufactured in accordance with known technology. Gas is thereby introduced into the fluid in the container. An outlet connection is also provided in the cap end wall. A relief valve, manufactured in accordance with known technology, is provided near the outlet connection so that gas accumulating in the container is vented if the gas leaving the outlet is impeded or stopped. Introduction of a dry gas into the container through the inlet connection and retrieval of a humidified gas through the outlet connection are accomplished through this two connection system.

In an alternative embodiment, substantially similar to the preferred embodiment, the camming ramp is positioned on the container neck and proportioned to flex the depending locking lug inwardly over the camming ramp and past the end stop. Once the locking lug advances past the end stop of the cam, it snaps radially outward engaging the locking relationship of lug and cam.

Two other embodiments of the present invention have at least one locking lug extending upwardly from the container neck. At least one camming ramp, which terminates in an end stop, projects from the cap skirt. The camming ramp is proportioned to flex the upwardly extending lug over the end stop as the cap is screwed onto the neck. One configuration of camming ramp flexes the lug radially outward, and the other configuration flexes the lug radially inward as the camming ramp passes over the lug. Once the end stop passes over the lug, it snaps back and the locking relationship is engaged.

BRIEF DESCRIPTION OF THE DRAWINGS

For a more complete understanding of this invention, reference should now be had to the embodiments illustrated in greater detail in the accompanying drawings.

In the drawings:

FIG. 1 is a perspective view of the non-refillable humidifier container, capped and in its locked closed condition, showing the cap with inlet and outlet connections.

FIG. 2 is an elevational view, taken partly in section, of the top neck portion of a container and a cap of the closure system of this invention prior to threaded engagement with the container.

FIG. 3 is an elevational view of the top portion of a container and a cap of the closure system after screw engagement with the container and in a locked position.

FIG. 4 is a cross section of the closure system's cap and container neck taken along line 4—4 of FIG. 3.

FIG. 5 is a perspective view of the top portion of a container and a cap of the closure system prior to screw engagement with the container.

FIG. 6 is a cross section, similar to FIG. 4, showing another embodiment of the closure system's cap and container neck.

FIG. 7 is a perspective view of the top portion of a container and a cap of another embodiment of the closure system prior to screw engagement with the container.

FIG. 8 is a cross section, similar to FIG. 4, showing the embodiment of the system's cap and container neck shown in perspective in FIG. 7.

FIG. 9 is a cross section, similar to FIG. 4, showing yet another embodiment of the system's cap and container neck.

DESCRIPTION OF THE PREFERRED EMBODIMENTS

Turning now to the drawings, FIG. 1 is a perspective view of a non-refillable humidifier container 10 embodying the closure system of this invention. Cap 14 includes inlet connection 16 and outlet connection 18 and depending lugs 30, 32. Gas permeable dip tube 17 is shown in phantom. FIG. 5 shows the top, neck portion 12 of the container having external threads 20. Neck portion 12 defines container outlet 34. Camming ramp 36 having end stop 42 is also shown on neck portion 12. Also shown in FIG. 5 is cap 14. Cap skirt 26 terminates in open end 28. Depending lugs 30, 32 extend downwardly from open end 28 of skirt 26. Cap 14 has internal threads 22.

FIG. 2 shows neck portion 12 of container 10 and cap 14, which comprise the closure system, prior to threaded engagement. Neck 12 has external threads 20 which cooperate with internal threads 22 on cap 14. Cap 14 also has an annular sealing gasket 24 to insure a tight seal between cap 14 and neck 12. Cap skirt 26 terminates in open end 28 to cover neck portion 12 of container 10. Depending lugs 30, 32 extend downwardly from the open end 28 of skirt 26. One of the camming ramps, camming ramp 36, is located on neck 12 just below threads 20.

FIG. 3 shows the sealing system in its closed position where cap 14 threadedly engages neck 12 of container 10. In this closed and locked position, cap 14 cannot be unscrewed from neck 12. FIG. 4 illustrates the operation of the closure system. Lugs 30a, 32a are shown in phantom and represent lugs 30, 32 in their cammed-out intermediate position. As cap 14 is rotated in a clockwise direction, indicated by arrows 13, 15, lugs 30a, 32a are cammed, respectively, by camming ramps 35 and 36. Lugs 30a, 32a flex radially outward as cap 14 is screwed onto the neck 12. Once lugs 30a, 32a are out of camming relation with camming ramps 35 and 36, the lugs 30a, 32a snap radially inwardly after passing over end stops 40, 42 on cams 35, 36. If an attempt is made to remove cap 14 by rotating in a counterclockwise direction, as shown by arrows 19, 21, end stops 40, 42 on cams 35, 36 are contacted by lugs 30, 32. End stops 40, 42 have a rachet type effect and drive lugs 30, 32 radially inward preventing any further rotational movement of lugs 30, 32 and hence preventing cap 14 from being removed. Lugs 30, 32 are strong enough to be substantially free of tangential flex, so that they cannot be forced over the cams. Cap 14 is preferably strong enough to resist inward lateral deflection of a type to cause outward lateral deflection of locking lugs 30, 32 under hand squeezing force. That is, squeezing of the cap will not alter the locking relationship of the lugs and the camming ramps.

Operation of an alternative embodiment is shown in FIG. 6. This embodiment is substantially the same as the embodiment illustrated in FIG. 4 except as otherwise described herein. Lugs 46a, 48a are shown in phantom and represent lugs 46, 48 in their cammed-out intermediate position. As the cap is rotated in a clockwise direction, indicated by arrows 50, 52, lugs 46a, 48a, are cammed by camming ramps 54, 56 on container 10a. Lugs 46a, 48a flex radially inward as the cap is screwed onto the neck. Once lugs 46a, 48a are out of camming relation with camming ramps 54, 56, lugs 46a, 48a snap radially outwardly after passing over end stops 58, 60 on cams 54, 56. If an attempt is made to remove the cap by rotating in a counterclockwise direction, as shown by arrows 53, 55, end stops 58, 60 on cams 54, 56 are contacted by lugs 46, 48. End stops 58, 60 prevent any further movement of lugs 46, 48 and hence prevent the cap from being removed. Lugs 46, 48 are strong enough to be substantially free of tangential flex so that they cannot be forced over the cams. The cap is preferably strong enough to resist outward lateral deflection of a type to cause inward lateral deflection of locking lugs 46, 48 under hand squeezing force. That is, squeezing of the cap will not alter the locking relationship of the lugs and the camming ramps.

FIG. 7 shows another alternative embodiment which is substantially the same as the embodiment illustrated in FIG. 5 except as otherwise described herein. FIG. 7 shows the top, neck portion 12a of the container having external threads 20a. Neck portion 12a defines container outlet 34a. Lug 62, one of the two locking lugs, extends upwardly from neck portion 12a. Cap 14a is also shown with cap skirt 26a terminating in open end 28a. Cap 14a has internal threads 22a. Cams 68, 70 project from open end 28a of skirt 26a.

The cross sectional view of FIG. 8 illustrates the operation of the embodiment of the closure system of FIG. 7. Camming ramps 68a, 70a are shown in phantom and represent camming ramps 68 and 70 after they have cammed locking lugs 62, 63. As cap 14a is rotated in a clockwise direction, indicated by arrows 72, 74, camming ramps 68, 70 cam locking lugs 62, 63. Lugs 62, 63 flex radially inward as cap 14a is screwed onto neck 12a. Once lugs 62, 63 are out of camming relation with camming ramps 68, 70, lugs 62, 63 snap radially outward after end stops 76, 78 on camming ramps 68, 70 have passed over them. If an attempt is made to remove cap 14a by rotating in a counterclockwise direction, as shown by arrows 73, 75, end stops 76a, 78a—the phantom depiction of the camming ramps—contact lugs 62, 63. Lugs 62, 63 prevent any further movement of camming ramps 68a, 78a and hence prevent cap 14a from being removed. Lugs 62, 63 are strong enough to be substantially free of tangential flex so that the camming ramps cannot be forced over them. Cap 14a is preferably strong enough to resist inward lateral deflection of a type to cause outward lateral deflection of camming ramps 68, 70 under hand squeezing force of cap 14a. Squeezing the cap will not alter, that is disengage, the locking relationship of the lugs and the camming ramps.

The operation of still another embodiment, having camming ramps projecting from the cap of the closure system and locking lugs upwardly directed from the neck of the container, is illustrated in FIG. 9. Except as otherwise described herein, the embodiment shown in FIG. 9 is substantially the same as the embodiment illustrated in FIG. 8. Lugs 62a, 63a are located on the neck of container 10c. Camming ramps 80, 82 are located on the cap of the closure system. The phantom representations of camming ramps 80a, 82a show the camming ramps after they have passed over lugs 62a, 63a respectively.

As the cap is rotated in a clockwise direction, indicated by arrows 81, 83, lugs 62a, 63a are cammed by camming ramps 80, 82. Lugs 62a, 63a flex radially outward as the cap is screwed onto the neck. Once lugs 62a, 63a are out of camming relation with camming ramps 80, 82, the lugs 62a, 63a snap radially inward after end stops 84, 86 on cams 80, 82 have passed over lugs 62a, 63a. If an attempt is made to remove the cap by rotating it in a counterclockwise direction, as shown by arrows 85, 87, end stops 84a, 86a—in the phantom depiction of camming ramps 80a, 82a—contact lugs 62a, 63a. This prevents any further movement of camming ramps 80a, 82a and hence prevents the cap from being removed. Lugs 62a, 63a are strong enough to be substantially free of tangential flex so that the camming ramps cannot be forced over them. The cap is preferably strong enough to resist inward lateral deflection of a type to cause outward lateral deflection of camming ramps 80 and 82 under hand squeezing force which could allow the camming ramps of a locked cap to pass over the lugs.

The above has been offered for illustrative purposes and is not intended to limit the invention of this application, which is defined in the claims below.

What is claimed is:

1. A closure system for a non-refillable, humidifier container, said container including a neck defining a container outlet and said neck being externally threaded, and a cap having internal threads carried in rotatable threaded cooperation with the threads on the neck, the improvement comprising:

said cap defining a skirt having an open end, said skirt having at least one locking lug extending downwardly from the open end of said skirt, an inlet connection through an end wall of said cap having means for introducing a gas into a fluid contained in said container, an annular sealing gasket on said end wall of said cap, and said end wall defining an opening comprising an outlet connection in said end wall of said cap; and, said container neck defining at least one camming ramp terminating at an end stop for camming said locking lug over said end stop, whereby rotation of said cap is prevented only by contact of said lug with said end stop when said cap is attempted to be removed.

2. The closure system of claim 1 wherein said camming ramp being proportioned to flex said locking lug radially outward as said cap is screwed onto said neck, and to permit said locking lug to snap radially inward when out of camming relation with the camming ramp.

3. The closure system of claim 1 wherein said camming ramp being proportioned to flex said locking lug radially inward as said cap is screwed onto said neck, and to permit said locking lug to snap radially outward when out of camming relation with the camming ramp.

4. The closure system of claims 1, 2 or 3 wherein said locking lugs are strong enough to be substantially free of tangential flex when contacting said end stops with a user attempting to remove said cap under hand force.

5. The closure system of claim 2 wherein said cap being strong enough to resist inward lateral deflection of a type to cause an outward lateral deflection of said locking lugs with a user attempting to remove said cap under hand force.

6. The closure system of claim 3 wherein said cap being strong enough to resist outward lateral deflection of a type to cause inward lateral deflection of said locking lugs with a user attempting to remove said cap under hand force.

7. A closure system for a pre-filled, non-refillable humidifier container for inhalation therapy, said container including a neck defining an outlet and said neck being externally threaded, and a cap having internal threads carried in rotatable threaded cooperation with the threads on the neck, the improvement comprising:

said cap defining a skirt having an open end, said skirt having at least two locking lugs extending downwardly from the open end of said skirt, an inlet through an end wall of said cap having means for introducing a gas into a respiratory therapy solution contained in said container, an annular sealing gasket on said end wall of said cap, and said end wall defining an opening comprising an outlet connection in said end wall of said cap for releasing humidified gas from said container, said cap being strong enough to resist inward lateral deflection of a type to cause an outward lateral deflection of said locking lugs with a user attempting to remove said cap under hand force; and, said container neck defining at least two camming ramps terminating at end stops for camming said locking lugs over said end stops, said camming ramps being proportioned to flex said locking lugs radially outward as said cap is screwed onto said neck, and to permit said locking lugs to snap radially inward when out of camming relation with the camming ramps, whereby rotation of said cap is prevented only by contact of said lugs with said end stops when said cap is attempted to be removed.

8. The closure system of claim 7 wherein said locking lugs are strong enough to be substantially free of tangential flex when contacting said end stops with a user attempting to remove said cap under hand force.

9. A closure system for a non-refillable container, said container including a neck defining a container outlet and said neck being externally threaded, and a cap having internal threads carried in rotatable threaded cooperation with the threads on the neck, the improvement comprising:
said container neck defining at least one locking lug extending upwardly from said container neck; and,
said cap defining a skirt having an open end, and said cap having at least one inlet connection through an end wall of said cap, said skirt having at least one camming ramp terminating at an end stop for camming said locking lug over said end stop, said camming ramp projecting from the open end of said skirt, whereby rotation of said cap is prevented only by contact of said lug with said end stop when said cap is attempted to be removed.

10. The closure system of claim 9 wherein said camming ramp being proportioned to flex said locking lug radially outward as said cap is screwed onto said neck, and to permit said locking lug to snap radially inward when out of camming relation with the camming ramp.

11. The closure system of claim 9 wherein said camming ramp being proportioned to flex said locking lug radially inward as said cap is screwed onto said neck, and to permit said locking lug to snap radially outward when out of camming relation with the camming ramp.

12. The closure system of claims 9, 10 or 11 wherein said inlet connection through said end wall is a gas permeable connection having means for introducing a gas into a fluid contained in said container, said end wall also defining an opening comprising an outlet connection in said end wall of said cap.

13. The closure system of claim 12 wherein said container of said closure system is filled with a humidifying solution.

14. A closure system for a non-refillable, humidifier container, said container including a neck defining a container outlet and said neck being externally threaded, and a cap having internal threads carried in rotatable threaded cooperation with the threads on the neck, the improvement comprising:
said container neck defining at least one locking lug extending upwardly from said container neck; and,
said cap defining a skirt having an open end, an inlet connection through an end wall of said cap having means for introducing a gas into a fluid contained in said container, an annular sealing gasket on said end wall of said cap, and said end wall defining an opening comprising an outlet connection in said end wall of said cap, said skirt of said cap having at least one camming ramp terminating at an end stop for camming said locking lug over said end stop, said camming ramp projecting from the open end of said skirt, whereby rotation of said cap is prevented only by contact of said lug with said end stop when said cap is attempted to be removed.

15. The closure system of claim 14 wherein said camming ramp being proportioned to flex said locking lug radially outward as said cap is screwed onto said neck, and to permit said locking lug to snap radially inward when out of camming relation with the camming ramp.

16. The closure system of claim 14 wherein said camming ramp being proportioned to flex said locking lug radially inward as said cap is screwed onto said neck, and to permit said locking lug to snap radially outward when out of camming relation with the camming ramp.

17. The closure system of claims 9, 10, 11, 14, 15 or 16 wherein said locking lugs are strong enough to be substantially free of tangential flex when contacting said end stops with a user attempting to remove said cap under hand force.

* * * * *